(12) United States Patent
Kim

(10) Patent No.: US 10,188,687 B2
(45) Date of Patent: Jan. 29, 2019

(54) ORIENTAL MEDICINAL COLLAGEN FOOD

(71) Applicant: Goo Whan Kim, Daejeon (KR)

(72) Inventor: Goo Whan Kim, Daejeon (KR)

(73) Assignee: Goo Whan Kim, Daejeon (KR)

( * ) Notice: Subject to any disclaimer, the term of this patent is extended or adjusted under 35 U.S.C. 154(b) by 100 days.

(21) Appl. No.: 15/633,348

(22) Filed: Jun. 26, 2017

(65) Prior Publication Data

US 2017/0304188 A1 Oct. 26, 2017

Related U.S. Application Data

(62) Division of application No. 14/794,361, filed on Jul. 8, 2015, now Pat. No. 9,717,677.

(30) Foreign Application Priority Data

Aug. 20, 2014 (KR) ........................ 10-2014-0108139

(51) Int. Cl.
| | | |
|---|---|---|
| A61K 36/00 | (2006.01) |
| A61K 36/23 | (2006.01) |
| A61K 8/98 | (2006.01) |
| A61K 8/97 | (2017.01) |
| A61Q 19/08 | (2006.01) |
| A61Q 19/00 | (2006.01) |
| C12P 1/00 | (2006.01) |
| A61K 36/28 | (2006.01) |

(52) U.S. Cl.
CPC ............... *A61K 36/23* (2013.01); *A61K 8/97* (2013.01); *A61K 8/981* (2013.01); *A61K 36/28* (2013.01); *A61Q 19/00* (2013.01); *A61Q 19/007* (2013.01); *A61Q 19/08* (2013.01); *C12P 1/00* (2013.01); *A61K 2800/85* (2013.01); *A61K 2800/92* (2013.01)

(58) Field of Classification Search
None
See application file for complete search history.

(56) References Cited

FOREIGN PATENT DOCUMENTS

| | | |
|---|---|---|
| KR | 100538688 | 12/2005 |
| KR | 1020070063096 | 6/2007 |
| KR | 1020130085497 | 7/2013 |
| KR | 101428363 | 8/2014 |

*Primary Examiner* — Qiuwen Mi

(74) *Attorney, Agent, or Firm* — IP & T Group LLP

(57) ABSTRACT

Oriental medicinal collagen food and manufacturing method of the oriental medicinal collagen food for skin beauty enhancement are provided. The manufacturing method including: a first process including: removing claws and scales from chicken feet, and preparing dandelion, *angelica gigas*, and *pueraria* root; a second process including: performing high-pressure pasteurization for the chicken feet obtained in the first process; a third process including: preparing dandelion extract by heating the dandelion in a bag; a fourth process including: obtaining Gyepogyo by heating and fermenting the pasteurized chicken feet and the dandelion extract in a pot; and a fifth process including: obtaining extract and distillate from a distillation of a mixture comprising the Gyepogyo, the *angelica gigas*, and the *pueraria* root.

8 Claims, 2 Drawing Sheets

ORIENTAL MEDICINAL COLLAGEN FOOD

CROSS-REFERENCE TO RELATED APPLICATIONS

This application is a divisional of U.S. patent application Ser. No. 14/794,361, filed on Jul. 8, 2015, which claims priority from and the benefit of Korean Patent Application No. 10-2014-0108139, filed on Aug. 29, 2014, each of which is hereby incorporated by reference in its entirety.

BACKGROUND

1. Field

Exemplary embodiments relate to oriental medicinal collagen food and manufacturing method thereof, and, more particularly to, oriental medicinal collagen food and manufacturing method of the oriental medicinal collagen food for skin beauty enhancement.

2. Discussion of the Background

Wrinkles are one of the most common symptoms caused by loss of moisture and elasticity resulting from skin aging. Among many theories regarding skin aging, some of which causes are diseases, stress, ultraviolet, and oxidative reactive species which also occurs during normal metabolism. These result in lipid peroxidation, protein oxidation, cutting and abnormal crosslinking of elastic fibers such as collagen and elastin chain, and melanin production. These lead to oxidative damage to cells and tissues, accelerating decrease in skin elasticity, wrinkles, melasma, freckles, and other skin aging symptoms. After climacteric period, women experience decrease in female hormone excretion, which leads to drastic decrease in biosynthesis ability of collagen including skin, especially dermis, resulting from low female hormone level. To prevent skin aging, reinforcement of collagen biosynthesis ability or building anti-oxidation defensive system to remove and suppress oxidative reactive species are necessary.

The connective tissues of dermis closely related to skin aging mainly include collagen and elastin. The main protein in the connective tissues, collagen, includes 70-80% of dry weight of dermis providing elasticity, strength, and maintains moisture. Decrease in collagen functionality from photoaging and intrinsic aging affects skin adversely by causing wrinkles, rough skin, less elasticity, dryness. As explained, collagen plays a vital role in maintaining skin elasticity and moisture, which would come from the proteins essential to cell generation. Therefore in dietetics, consumption of quality protein is closely related to skin health.

Edible cosmetic supplements are mainly collagen products extracted from fish, meat, and vegetables. Collagen is a type of fibrous protein, a main nutrient for formation of form muscular tissue, skin tissue, bone tissue, cartilage and cornea. Among the constituents of proteins, hydroxyproline, glycine, and serine have great effects on skin elasticity and moisture retention. Korean pharmaceutical or cosmetic companies sell collagen products made from imported collagen from United States and Japan. For example, Chung-Gye Pharmaceutical's 'Collagen Plus 3000,' Han-Mi Pharmaceutical's 'New Collagen,' Je-Il Pharmaceutical's 'Collagen 100,' and Citri's 'Collagen 1000' are all 100% or 99.9% made of imported collagens from the U.S. or Japan. Non-Korean products such as 'Collagen Gold' or 'Pure Collagen SD' are also made of pure collagen. Companies all over the world emphasize the collagen purity in selling their products. However, the problem lies on the lack of researches relating collagen consumption to increase in collagen content in human bodies.

In addition, there is another issue that the efficacy of edible collagen supplements is insufficiently proven objectively. There are not many researches whether consuming collagen increases the collagen contents in a human body. Korean Ministry of Food and Drug Safety (MFDS) keeps its stance at telling collagen can be used as a food ingredient but the relation between eating it and positive effect on skin is not scientifically proven.

Recently, collagen products with increased functionality by adding vitamin, beta-carotene, pomegranate, isopeulrabon from soybean, and others, are on market. 'Collagen Crystal 100' from Saerom Cosmetics is made of collagen from pork skin, 'Jeju Horse Placenta Collagen' is literally condensed from horse placenta, and low Molecular Weight Fish Collagen' from Amore Aritaum has fish collagen raw compound outside of Korea. There are other products with collagen from stingrays, shark's fin, pig placenta or skin, or sheep placenta.

To strengthen connective tissues like muscle, skin, and bones, a traditional way Koreans used to consume collagen is making gelatin from heating animals or fishes with high collagen content followed by fermenting them. Collagen becomes viscous gelatin when heated. They consumed it in glue state for easy storage. The examples of edible glue are glue from donkey skin, glue made with antlers, glue from tortoise shell, glue from snapping turtle shell. Since these materials were expensive and hard to procure, they used chicken feet, which can be easily and massively purchased, to prepare gel from boiling. Other traditional ways of efficiently consuming collagen were eating fermented skates or cow knee knucklebone soup.

As explained, traditional ways of consuming collagen is deficient of proven efficacy from accurate clinical trials, and without examples or prescription specifically meant for skin health improvement. It is difficult to assess an appropriate price based on efficacy, not knowing why such high price has to be paid. Korean Patent No. 10-1361060, issued to University-Industry Cooperation Foundation at Konkuk University in Korea (Title of invention "Method of Collagen Extraction from Chicken Residual Parts"), maximizes extraction efficiency with swelling chicken skin in acid and alkali, controlling pH to edible range with neutralization, removing odor and unwanted ingredients with hot-water extraction, and prepare granulized collagen with freeze-dry for easy utilization. Korean Patent No. 10-0733081, issued to Hankook Foodifarm Co., describing a method of preparing chondroitin sulfuric acid from chicken feet consist of heated extraction, centrifuge, condensation or condensing the top part from centrifuge after hydrolysis with proteolytic enzyme and inactivating the enzyme. The method to prepare nutrition boost extract and jelly involves boiling chicken feet with atractylodes, amomum anthioides wallich, and other gastrointestinal supplements. Korea Food Research Institute obtained collagen by sonicating from fish skin. There is another way to prepare collagen product from collagen with molecular weight around 30,000-50,000 from a low-temperature and low molecular weight process.

However, the above mentioned products for edible beauty supplements do not produce sufficient collagen in a human body. Other processes that extract collagen from animal only try producing active ingredients using strong acids, hydrolysis, or boiling animal parts with oriental medicines helping digestion. These involve very complex procedures and produce a lot of industrial waste due to use of strong acid. Lack of theoretical evidence regarding collagen digestion and biosynthesis in a human body is another problem. The above information is only for enhancement of understanding of the background of the inventive concept. Thus, it may contain information that does not constitute the prior art that is already known to a person having ordinary skill in the art.

SUMMARY

Exemplary embodiments disclose an oriental medicinal collagen food for skin beauty enhancement prepared with chicken feet, dandelion, *angelica gigas*, and *pueraria* root as main ingredients, and a method of manufacturing thereof.

An exemplary embodiment discloses a manufacturing method including: a first process including: removing claws and scales from chicken feet, and preparing dandelion, *angelica gigas*, and *pueraria* root; a second process including: performing high-pressure pasteurization for the chicken feet obtained in the first process; a third process including: preparing dandelion extract by heating the dandelion in a bag; a fourth process including: obtaining Gyepogyo by heating and fermenting the pasteurized chicken feet and the dandelion extract in a pot; and a fifth process including: obtaining extract and distillate from a distillation of a mixture comprising the Gyepogyo, the *angelica gigas*, and the *pueraria* root.

An exemplary embodiment also discloses an oriental medicinal collagen food for skin beauty enhancement including: Gyepogyo comprising a fermented mixture of pasteurized chicken feet and dandelion extract, wherein claws and scales are removed from the pasteurized chicken feet; and at least one of *angelica gigas* and *pueraria* root.

To resolve the aforementioned problems, oriental medicinal collagen food for skin beauty enhancement may be prepared with natural ingredients such as chicken feet, dandelion, *angelica gigas*, and *pueraria* root to increase affinity to a human body. Along with one or more exemplary embodiments described herein, other methods and processes may be used to prepare gelatin collagen for increased absorption to body.

DETAILED DESCRIPTION OF THE ILLUSTRATED EMBODIMENTS

Figure 1:
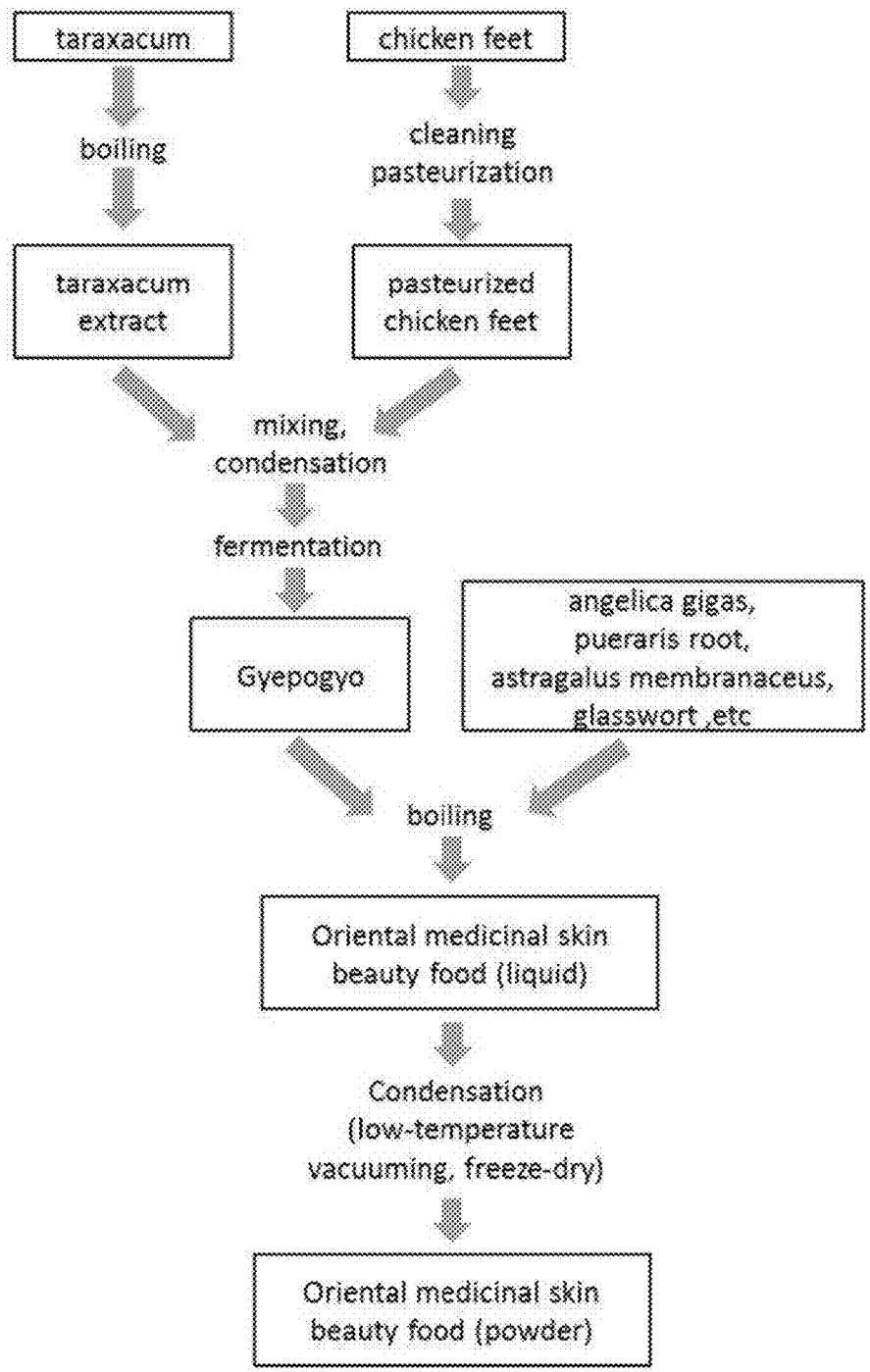
FIG. 1 is a flowchart illustrating a manufacturing method of oriental medicinal collagen food for skin beauty enhancement prepared with chicken feet, dandelion, *angelica gigas*, and *pueraria* root as main ingredients.

Exemplary embodiments will be described more fully hereinafter with reference to the accompanying drawings, in which exemplary embodiments of inventive concept are shown. Throughout the drawings and the detailed description, unless otherwise described, the same drawing reference numerals are understood to refer to the same elements, features, and structures. In describing the exemplary embodiments, detailed description on known configurations or functions may be omitted for clarity and conciseness.

Exemplary embodiments disclose a manufacturing method of oriental medicinal collagen food for skin beauty enhancement prepared with chicken feet, dandelion, *angelica gigas*, and *pueraria* root as main ingredients.

An exemplary embodiment provides affordable and easy-to-use oriental medicinal collagen food for skin beauty enhancement. This can be done by enabling safe and mass production through the optimal combination of herbal medicine with ample amino acids and herbal medicine rich with vegetable female hormone that helps collagen biosynthesis in a human body.

To achieve the above-mentioned objective, the manufacturing method of oriental medicinal collagen food for skin beauty enhancement prepared with chicken feet, dandelion, *angelica gigas*, and *pueraria* root as main ingredients may include the following processes: a first process: a) cleaning chicken feet with potable water, removing claws and scales, and thoroughly cleaning the chicken feet with high-pressure hot water blaster to remove other unwanted materials, and b) preparing dandelion, *angelica gigas*, and *pueraria* root, and, optionally, other oriental medicinal ingredients; a second process: applying high-pressure pasteurization to the chicken feet prepared through the first process; a third process: preparing dandelion extract by heating the dandelion in a bag made of hemp cloth or a similar bag; a fourth process: preparing Gyepogyo by heating and fermenting the mixture of the pasteurized chicken feet and the dandelion extract previously prepared in a large pot; a fifth process: mixing Gyepogyo with the prepared *angelica gigas* and *pueraria* root while extract and post-distillation residual liquid from one or more of the prepared oriental medicinal ingredients are prepared in a large pot or pharmaceutical distillatory; a sixth process: preparing granules by drying the extract obtained from the fifth process with low-temperature vacuum condenser or dry-freezer.

The other oriental medicinal ingredients may include at least one of *astragalus membranaceus*, *lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint.

Further, the previously mentioned third process may include preparing the dandelion extract by mixing the dandelion with *angelica gigas*, *pueraria* root, and one or more of the following oriental medicinal ingredients; *astragalus membranaceus*, *lycium* barbarum, *astragalus membranaceus*, *lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint.

The oriental medicinal collagen food may increase provision of essential amino acids with chicken feet collagen and anti-inflammatory function from dandelion. This positively affects skin elasticity and moisture retention from enhanced bodily absorption when taken by consumers.

Chicken feet and dandelion are common natural ingredients. The manufacturing processes are also economical due to low cost and relatively easy processes.

Further, the oriental medicinal collagen food for skin beauty enhancement can be used as protein supplement for dietary weight control, blood circulation facilitation for fatigue recovery, drinking cosmetics boosting collagen biosynthesis, powder cosmetics easy for taking internally and applying on skin, oriental medicine for musculoskeletal system, and curing agent for aridness, atopy, and dry skin.

The main ingredients in this oriental medicinal collagen food for skin beauty enhancement may include collagen, chicken feet, dandelion, *angelica gigas*, and *pueraria* root.

Their main nutrients, efficacy, main oriental medicinal theory are explained hereinafter.

Collagen: 25 percent of proteins in a human body is collagen. Collagen is the main substance for connective tissues such as bone, tendon, and muscle. Collagen forms a truss with its three branches of polymer protein bound strongly. It is not soluble to water, weak acid, or weak alkali, but becomes gelatin when boiled. The known efficacy of collagen is for osteoporosis, knee arthritis, brain development, skin beautification, moisture retention, increase in immunity, growth and development, arteriosclerotic, hemostasis, and vision improvement. Amino acids in collagen are proline, oxyproline, glycine, and glutamic acid. Pig feet, broth from boiled cow bones, chicken feet, pig skin, cow knee knucklebone soup contain high concentration of collagen.

Chicken feet: chicken feet include bone, joint, cartilage, tendon, and muscle, rich in potassium, marrow, protein, collagen, and other trace elements. Collagen is fibrous proteins including amino acids, which is mostly found in outer layer of organs, cartilage, teeth, hair, muscle, and skin. It strengthens joints. Chicken feet are not thick and in cartilage form. Cartilage parts has chondroitin, skin has glycoprotein such as glycine and protein for connective tissues such as collagen or elastin. Considerable mass of extracellular materials exists between connective tissues, and the species and array of these materials specify connective tissue proper, cartilage, bone, and blood. Among connective tissue proper, dermis is a loose connective tissue with dispersed collagen, a kind of fibrous collagen. Tendons connect muscles and bones, and are dense connective tissues with collagen densely arrayed in a regular or irregular manner. Chicken feet have been known for a long time to be good for degenerative joint arthritis. Its recently discovered beneficial effect on skin beautification and lowering blood pressure is due to increase in physiological activity from these nutrients.

Dandelion: taraxacums are perennial plants in astrales order. Different taraxacums are *Taraxacum* nonogolicum H. Mazz, *Taraxacum* ohwianum Kitamura, *Taraxacum* coreanum Nakai, and *Taraxacum officinale* Weber. They are used to remedy acute hepatitis, reinforce immune systems, protect liver, promote urination, and remedy mastitis, throat inflammation, swelling due to fever. They have 17 of all proteinogenic amino acids except cysteine, and other 8 essential amino acids. They are 1.4 to 1.8 times more abundant in leaves than roots. The leaves contain the following main constituents in order of its contents; glutamic acid, proline, phenylalanine, aspartic acid, arginine, leucine, lysine. Inorganics such as potassium and calcium are abundant along with magnesium, manganese, and iron.

*Angelica gigas*: *angelica gigas* are commonly used for blood-related disease because it promotes blood production. *Angelica gigas* Nakai, *Angelica sinensis* (Oliv.) Diels, *Angelica acutiloba* (Sieb. & Zuc) Kitagawa are commonly used. They promote blood flow in coronary arteries and production of red blood cells. The encyclopedia of basic agricultural plants of ancient China describes it tastes sweet, has warm traits, is not poisonous, warms body, stops pain, cure arthritis, are used when a pregnant woman has a sign of miscarriage or on their skin problems, protects five viscera, generates tendons and muscle. According to Compendium of Materia *Medica, angelica gigas* controls blood, is good for womanhood. They cure palsy, chi malfunction, and fatigue. They also remove bad blood and produce fresh blood. They are good for habitual constipation, menstruation and other postpartum symptoms. A research tells they prevent loss of bone tissues by inhibiting the differentiation of osteophage. Decursinol in them is for pain-relieving, decursin for anticancer, angelan for anti-diabetes. They promote red blood cell production and protein synthesis. They are anti-inflammatory, pain-relieving.

*Pueraria* root: The levels female hormone related to biosynthesis of collagen in a human body plummet after menopause. The collagen cosmetics released recently in the market contain vegetable female hormone from pomegranate or isopeulrabon from soybean. One research, however, showed *pueraria* root has 600 times more vegetable female hormone than pomegranate.

Hereinafter, a manufacturing method of oriental medicinal collagen food for skin beauty enhancement will be described with reference to FIG. 1.

FIG. 1 is a flowchart illustrating a manufacturing method of oriental medicinal collagen food for skin beauty enhancement prepared with chicken feet, dandelion, *angelica gigas*, and *pueraria* root as main ingredients.

The First Process: Ingredients Preparation

In the first process, chicken feet are cleaned with potable water, claws and scales are removed from the chicken feet, and then the chicken feet are thoroughly cleaned with high-pressure hot water blaster to remove other unwanted materials from the chicken feet. Also, dandelion, *angelica gigas, pueraria* root, and other oriental medicinal ingredients are prepared.

Although it may be omitted or modified, it is preferred that the chicken feet are cleaned with potable water, removed of claws and scales, and thoroughly cleaned with high-pressure hot water blaster to remove other unwanted materials.

It is also recommended that dandelion, *angelica gigas, pueraria* root, and other oriental medicinal ingredients are thoroughly cleaned.

The following ingredients, but not limited thereto, are examples of other oriental medicinal ingredients mentioned above; *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint.

The Second Process: Pasteurization

In the second process, the chicken feet prepared by the first process are heated in a water bath at 100-125° C., 1.5-2.5 atm for 10-30 minutes for high-pressure pasteurization.

It is recommended to kill the germs in and out of the chicken feet by heating the chicken feet prepared by the first process for high-pressure pasteurization at 100-125° C., 1.5-2.5 atm for 10-30 minutes. 121° C., 2 atm for 15 minutes are highly preferred.

The Third Process: Dandelion Extract Preparation

In the third process, the dandelion extract is prepared by heating dandelion prepared by the first process with potable water in a bag made of hemp cloth or a similar one at 80-125° C. for 60-180 minutes.

It is recommended that the above-mentioned dandelion is placed in a bag of hemp cloth or a similar one. The material for the bag is recommended to be of natural origin that does not release any harmful substances when heated.

It is preferred that the dandelion is heated in a water bath with potable water after placed in the bag of hemp cloth or similar at 80-125° C., 1-2.5 atm for 60-180 minutes to prepare the extract. It is highly recommended that the dandelion is extracted at 80-90° C. and is heated for 90-120 minutes after it reaches the recommended temperature.

The weight of the potable water for extraction is recommended to be 15-20 times more than that of dandelion.

The other oriental medicine prepared in the first process may include one or more of *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint. They are placed in the water bath along with the dandelion, then heated at 80-125° C., 1-2.5 atm for 60-180 minutes to prepare the mixed extract. The weight of the potable water for extraction is recommended to be 9-15 times more than weights of dandelion and the other oriental medicine.

The Fourth Process: Preparation of Gyepogyo

In the fourth process, Gyepogyo is produced by boiling the pasteurized chicken feet from the second process and the dandelion extract from the third process in a large kettle at 60-99.9° C. for 24-72 hours.

The pasteurized chicken feet prepared by the second process and the dandelion extract prepared by the third process are mixed in the weight ratio of 1:1.2 to 1:3, then boiled in a large kettle at 60-99.9° C. for 24-72 hours. The weight of the dandelion is recommended to be 1.2-2 times higher than that of the chicken feet. It is highly recommended that the dandelion extract, 1.5 times more than the chicken feet by weight, are heated while loss from the evaporation is continually compensate by adding more extracts.

The total heating time to prepare Gyepogyo can be longer than 24-55 hours if more time is needed to turn the product into glue. Heated condensation at medium heat for 30-48 hours after the mixture first boils is highly recommended while adding more dandelion extract as it evaporates.

It is recommended that the fat forming during the heating process be removed while adding more dandelion extract as it evaporates. The product is packaged after removing residual bones and parts, adding fermenting liquid at room temperature, fermenting at 30 55° C. for 10-60 hours, and high pressure pasteurization at 110-125° C. The fermenting liquid can be any that satisfies food safety regulations.

The Fifth Process: Preparation of Post-Distillation Residual Liquid and Extract

In the fifth process, post-distillation residual liquid and extract are prepared by adding *angelica gigas* and *pueraria* root obtained from the first process to Gyepogyo prepared by the fourth process, followed by placing this mixed Gyepogyo and one or more of the other oriental medicine obtained from the first process in a pharmaceutical distillatory.

The other oriental medicine mentioned above may include one or more of *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint to be placed in a large kettle or a pharmaceutical distillatory.

The Gyepogyo obtained from the above mentioned processes may be placed in the bath with potable water together with oriental medicinal nutrients efficacious as oriental medicinal collagen skin beauty food including *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint. Then, they are heated at 80-125° C., 1-2.5 atm for 60-220 minutes to obtain extract. This extract can be used after packaged in pouches or containers. Distillate from the extract can be obtained with a pharmaceutical distillatory.

The Sixth Process: Drying and Packaging

In the sixth process, granules may be produced by drying the post-distillation residual liquid and extract obtained from the fifth process with vacuum condensation or freeze-dry.

It is recommended that the extract obtained from the fifth process is condensed in a low-temperature vacuum condenser, mixed with excipients, dried to produce solid powder.

After solidification through freeze-drying, it is recommended that the product be prepared into spheres, granules, pills, or capsules.

The liquid extract produced from boiling or distillation as in the fifth process may be used without the sixth process.

Further, according to an exemplary embodiment, a manufacturing method of oriental medicinal collagen food for skin beauty enhancement is prepared with chicken feet, dandelion, *angelica gigas*, and *pueraria* root as main ingredients. First, cleaned chicken feet is pasteurized in a water bath at high-pressure, and dandelion extract is prepared. Gyepogyo is then obtained by heating the pasteurized chicken feet and the dandelion extract in a large kettle, and Gyepogyo is mixed with *angelica gigas* and *pueraria* root after the heating. One or more of the aforementioned oriental medicinal ingredients are further mixed and heated in a large kettle or a pharmaceutical distillatory to prepare extract and post-distillation residual liquid. The extract is dried in a low-temperature vacuum condenser to prepare dry spherical solid.

The oriental medicinal collagen food enhances the anti-inflammatory function of dandelion and provision of essential amino acids with chicken feet collagen ingredients by manufacturing oriental medicinal collagen food for skin beauty enhancement prepared with chicken feet, dandelion, *angelica gigas*, and *pueraria* root as main ingredients. It is also to maintain moist and smooth skin, and increase skin elasticity by facilitating the absorption to a human body when consumers take this food.

Moreover, since chicken feet and dandelion are natural nutrients, and the overall manufacturing cost is low and economical.

The following examples explain one or more exemplary embodiments in more detail. These examples and exemplary embodiments are for illustration purpose only, without limiting the scope of the claims.

Exemplary Embodiment 1

1. The First Process: Ingredients Preparation

Chicken feet were washed with potable water. After the first cleaning process, claws and scales were removed from the chicken feet, and then the chicken feet were thoroughly cleaned with high-pressure hot water blaster. From various sources, e.g., dried food vendors and oriental medicinal herbal vendors, dandelion, *pueraria* root, *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, peppermint, and other ingredients were obtained.

2. The Second Process: Pasteurization 10 kg of the cleaned chicken feet were heated in a water bath at 121° C., 2 atm for 15 minutes for high-pressure pasteurization.

3. The Third Process: Dandelion Extract Preparation 24 kg of dandelion extract was obtained by boiling 4 kg of dandelion in a hemp cloth bag with 40 liter of water at 80-100° C. for 60-180 minutes in a water bath. The weight of the solvent was kept at 15-20 times that of dandelion while extracting.

4. The Fourth Process: Gyepogyo Production 10 kg of the pasteurized chicken feet and 15 liter of dandelion extract were placed in a large kettle together, and the temperature was kept at 80-99.9° C. for 24-72 hours. They were then fermented for 30-50 hours at 40-55° C. The product was pasteurized at 110-125° C. to produce 7.5 liter of Gyepogyo.

5. The Fifth Process: Extract Production Gyepogyo 250 g, *angelica gigas* 100 g, *pueraria* root 80 g, *astragalus membranaceus* 100 g, *lycium* barbarum 60 g, *ligusticum* wallichii 60 g, white *paeonia lactiflora* 60 g, matured rehmannia *glutinosa* 60 g, spirodela polyrhiza 60 g, white *imperata* cylindrical 100 g, longan 80 g, houttuynia *cordata* 60 g, dried *Artemisia* 60 g, glasswort 60 g, tender branch of cinnamon 60 g, *glycyrrhiza uralensis* 50 g, black bean 80 g, Job's tears 80 g, saururi herba 60 g, and peppermint 40 g were heated with 14 liter of potable water in a pharmaceutical distillatory at 90-105° C. for 100-200 minutes to produce 2.5 liter of distillate and 10 liter of extract. If no distillate is needed, a common kettle can be used.

6. The Sixth Process: Drying and Packaging 12 liter of the extract obtained from the fifth process was condensed in a low-temperature vacuum condenser for 6 hours to produce 285 grams of oriental medicinal collagen skin beauty food powder. It was packaged into 100 pouches for 2.8 g each. The extract from low-temperature vacuum can be produced into powder with excipients.

Exemplary Embodiment 2

1. The First Process: Ingredients Preparation

Chicken feet were washed with potable water. Claws and scales were removed from the chicken feet, and the chicken feet were thoroughly cleaned with high-pressure hot water blaster. From various sources, e.g., dried food vendors and oriental medicinal herbal vendors, dandelion, *pueraria* root, *astragalus membranaceus, lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, peppermint, and other ingredients were obtained.

2. The Second Process: Pasteurization 10 kg of the cleaned chicken feet were heated in a water bath at 121° C., 2 atm for 15 minutes for high-pressure pasteurization.

3. The Third Process: Mixed Dandelion Extract Preparation 4 kg of dandelion was placed in a hemp cloth bag along with *angelica gigas* 100 g, *pueraria* root 80 g, *astragalus membranaceus* 100 g, *lycium* barbarum 60 g, *ligusticum* wallichii 60 g, white *paeonia lactiflora* 60 g, matured rehmannia *glutinosa* 60 g, spirodela polyrhiza 60 g, white *imperata* cylindrical 100 g, longan 80 g, houttuynia *cordata* 60 g, dried *Artemisia* 60 g, glasswort 60 g, tender branch of cinnamon 60 g, *glycyrrhiza uralensis* 50 g, black bean 80 g, Job's tears 80 g, saururi herba 60 g, and peppermint 40 g. The bag and 40 liter of potable water was heated at 80-100° C. for 60-180 minutes in a water bath to produce 24 liter of dandelion extract. The weight of the solvent was 9-15 times that of medicinal herbal ingredients while mixed dandelion extract was being produced.

4. The Fourth Process: Gyepogyo Production 10 kg of the pasteurized chicken feet and 15 liter of dandelion and herbal medicine extract obtained from the third process were placed in a large kettle together, and the temperature was kept at 80-99.9° C. for 24-72 hours. They were then fermented for 30-50 hours at 40-55° C. The product was pasteurized at 110-125° C. to produce 7.5 liter of Gyepogyo.

5. The Fifth Process: Extract Production 7.5 liter of Gyepogyo from the fourth process was dried with a low-temperature vacuum condenser to produce 850 g of oriental medicinal collagen skin beauty food powder. 170 pouches with Gyepogyo with 5 g each were prepared.

The oriental medicinal collagen skin beauty food, which is the mixture of the individual extracts from high-protein and anti-oxidative foods, has beneficial effects on skin elasticity, moisture retention, wrinkle, and pores. The reason for protein content increase is thought to be due to the fact that the main ingredient, the chicken feet, dandelion, *angelica gigas, pueraria* root, accelerated the protein biosynthesis and absorption in a human body. Significant differences were shown in moisture, elasticity, pores, wrinkles, and other items before and after the consumption.

In addition, the increase in bodily water content, skin moisture increase, and reduction in pore size were verified after the consumption of the oriental medicinal collagen skin beauty food. This shows that the vegetable protein in *pueraria* root has a close relation with skin elasticity, pore, wrinkle, and moisture retention.

Experiment 1: Measurement of Hydroxyproline Content.

Hydroxyproline is the characteristic protein in collagen and the gelatin.

Figure 2:
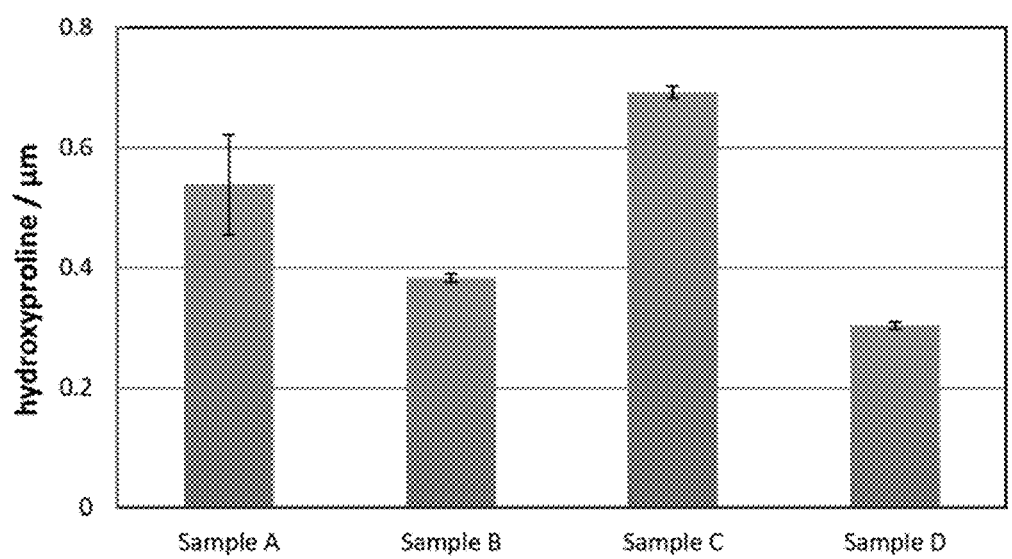
FIG. 2 illustrates hydroxyproline contents in four collagen products.

FIG. 2 illustrates hydroxyproline contents in four collagen products.

TABLE 1

Hydroxyproline contents in four collagen products

|  | Sample A | Sample B | Sample C | Sample D |
|---|---|---|---|---|
| Mean | 0.539111 | 0.383147 | 0.692833 | 0.303793 |
| Standard Deviation | 0.08328 | 0.006864 | 0.010135 | 0.00595 |

As shown in FIG. 2 and Table 1, Sample C according to an exemplary embodiment has the most hydroxyproline than the other three comparative examples. The other three comparative examples are other collagen enhancement foods.

Experiment 2

TABLE 2

General content analysis of the product according to an exemplary embodiment

| Item No. | Product Name | Analyzed Item | Results | | Remarks |
|---|---|---|---|---|---|
| 15-209 | Gyepogyo | Water Content | 91.48 | g/100 g | ±0.00 |
| 15-210 | | Ash | 1.03 | g/100 g | ±0.03 |
| 15-211 | | Crude Fat | 0.21 | g/100 g | ±0.03 |
| 15-212 | | Crude Protein | 6.25 | g/100 g | ±0.04 |
| 15-213 | | pH | 5.01 | | ±0.01 |
| 15-214 | | Benzopyrene | 0.00 | µg/kg | |
| 15-215 | | Lead | 0.028 | mg/kg | ±0.00 |
| 15-216 | | Cadmium | Not detected | | |

In Gyepogyo product according to an exemplary embodiment, harmful metals or other harmful substances were not identified. Protein content result showed 30 times higher than fat. The acidity is pH 5.01, meeting the criteria for food materials.

What is claimed is:

1. An oriental medicinal collagen food for skin beauty enhancement comprising:
   a dried extract comprising:
      Gyepogyo comprising a fermented mixture of pasteurized chicken feet and dandelion extract, wherein claws and scales are removed from the pasteurized chicken feet; and
      at least one of *angelica gigas* and *pueraria* root.

2. The oriental medicinal collagen food of claim 1, wherein the dried extract is obtained from a distillation of a mixture of the Gyepogyo, the *angelica gigas*, and the *pueraria* root.

3. The oriental medicinal collagen food of claim 2, wherein the mixture further comprises an oriental medicinal ingredient, and
   wherein the oriental medicinal ingredient comprises one or more of:
      *astragalus membranaceus*, *lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, or peppermint.

4. The oriental medicinal collagen food of claim 3, wherein an approximate weight ratio of the Gyepogyo, the *angelica gigas*, the *pueraria* root, and the oriental medicinal ingredient is set as about (25:10:8:113).

5. The oriental medicinal collagen food of claim 2, wherein the mixture further comprises an oriental medicinal ingredient comprising *astragalus membranaceus*, *lycium* barbarum, *ligusticum* wallichii, white *paeonia lactiflora*, matured rehmannia *glutinosa*, spirodela polyrhiza, white *imperata* cylindrical, longan, houttuynia *cordata*, dried *artemisia*, glasswort, tender branch of cinnamon, *glycyrrhiza uralensis*, black bean, Job's tears, saururi herba, and peppermint.

6. The oriental medicinal collagen food of claim 5, wherein an approximate weight ratio of the Gyepogyo, the *angelica gigas*, the *pueraria* root, and the oriental medicinal ingredient is set as about (25:10:8:113).

7. The oriental medicinal collagen food of claim 2, wherein the oriental medicinal collagen food is a dried granule-type food.

8. The oriental medicinal collagen food of claim 1, wherein an approximate weight ratio of the Gyepogyo, the *angelica gigas*, and the *pueraria* root is set as about (25:10:8).

* * * * *